United States Patent [19]

Grohe et al.

[11] Patent Number: 4,556,709

[45] Date of Patent: Dec. 3, 1985

[54] 2-AMINO-8-CYCLOPROPYL-5-OXO-5,8-DIHYDRO-PYRIDO[2,3-D]-PYRIMIDINE-6-CARBOXYLIC ACID COMPOUNDS

[75] Inventors: Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 401,684

[22] Filed: Jul. 26, 1982

Related U.S. Application Data

[63] Continuation of Ser. No. 111,057, Jan. 10, 1980, abandoned.

[30] Foreign Application Priority Data

Feb. 1, 1979 [DE]   Fed. Rep. of Germany ....... 2903850

[51] Int. Cl.⁴ .................. C07D 471/04; A61K 31/505

[52] U.S. Cl. .................... 544/117; 544/279; 544/323; 544/325; 544/329; 544/334; 260/243.3

[58] Field of Search ............... 544/279, 117; 260/243.3

[56] References Cited

U.S. PATENT DOCUMENTS

| | | | |
|---|---|---|---|
| 3,673,184 | 6/1972 | Minami et al. | 544/279 |
| 3,770,742 | 11/1973 | Matsumoto et al. | 544/279 |
| 3,887,557 | 6/1975 | Minami et al. | 544/279 |
| 3,950,338 | 4/1976 | Pesson | 544/279 |
| 3,992,380 | 11/1976 | Lesher et al. | 544/279 |
| 4,017,622 | 4/1977 | Minami et al. | 544/279 |

*Primary Examiner*—Glennon H. Hollrah
*Assistant Examiner*—James H. Turnipseed
*Attorney, Agent, or Firm*—Sprung Horn Kramer & Woods

[57] ABSTRACT

The invention relates to 2-amino-8-cyclopropyl-5-oxo-5,8-dihydropyrido[2,3-d]pyrimidine-6-carboxylic acid compounds, processes for their preparation and their use as antibacterial agents, and also as feed additives.

11 Claims, No Drawings

2-AMINO-8-CYCLOPROPYL-5-OXO-5,8-DIHYDRO-PYRIDO[2,3-D]-PYRIMIDINE-6-CARBOXYLIC ACID COMPOUNDS

This is a continuation of application Ser. No. 111,057, filed 1/10/80, now abandoned.

The present invention relates to new 2-amino-8-cyclopropyl-5-oxo-5,8-dihydropyrido[2,3-d]pyrimidine-6-carboxylic acid compounds, to processes for their production and to their use as antibacterial agents, and also as feed additives.

It has already been disclosed that 2-amino-8-ethyl-5-oxo-5,8-dihydro-pyrido[2,3-d]pyrimidine-6-carboxylic acids possess antibacterial properties [Eur. J. Med. Chem. 9, 591–596 (1974)].

According to the present invention there are provided compounds which are 2-amino-8-cyclopropyl-5-oxo-5,8-dihydropyrido[2,3-d]pyrimidine-6-carboxylic acids of the formula

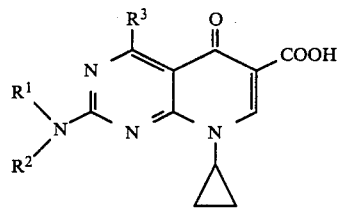

or a salt thereof in which $R^1$ and $R^2$ are identical or different and denote a hydrogen atom or a branched or unbranched $C_1$ to $C_{12}$ (preferably $C_1$ to $C_4$) alkyl, or $C_2$ to $C_{12}$ (preferably $C_2$ to $C_4$) alkenyl or alkynyl radical which is optionally substituted by one, two or more (preferably one or two) hydroxyl groups or alkoxy, alkylmercapto or dialkylamino groups which 1 to 3 carbon atoms per alkyl radical, a cyano group or an alkoxycarbonyl group with 1 to 4 carbon atoms in the alkoxy moiety or by an optionally substituted aryl radical or hetaryl radical, or denote a cycloalkyl radical with 3 to 6 (preferably 5 to 6) carbon atoms, or $R^1$ and $R^2$ together with the nitrogen atom on which they are substituents and optionally with a further heteroatom, for example, oxygen, sulphur, or $NR^4$, form a 3-membered to 7-membered ring, which is optionally mono-substituted or poly-(preferably di- or tri)substituted by $C_1$ to $C_6$ alkyl or $C_2$ to $C_6$ alkenyl groups, hydroxyl groups, alkoxy and alkylmercapto groups with 1 to 3 carbon atoms, an alkoxycarbonyl group with 1 to 4 carbon atoms in the alkoxy moiety, a cyano group or an optionally substituted aryl radical, and which optionally also possesses a double bond.

$R^3$ denotes a hydrogen atom, an alkyl group with up to 3 carbon atoms or an optionally substituted aryl radical and $R^4$ denotes a hydrogen atom or a branched or unbranched $C_1$ to $C_6$ alkyl or $C_2$ to $C_6$ alkenyl or alkynyl group optionally substituted by a hydroxyl group, an alkoxy, alkylmercapto or dialkylamino group with 1 to 3 carbon atoms per alkyl radical or an alkoxycarbonyl group with 1 to 4 carbon atoms in the alkoxy moiety, or denotes a cycloalkyl group with 3 to 7 (preferably 5 to 6) carbon atoms, an aralkyl group which has up to 4 carbon atoms in the aliphatic part and is optionally substituted in the aryl radical, denotes an optionally substituted phenyl or naphthyl group or a heterocyclic radical, such as, for example, a pyridine, pyrimidine, thiazole or benzthiazole nucleus, or denotes an alkoxycarbonyl group which has 1 to 4 carbon atoms in the alkoxy moiety and is optionally substituted by an optionally substituted aryl radical, or an alkanoyl radical with 1 to 6 carbon atoms, an aroyl radical, an optionally substituted alkyl- or aryl-(thio) carbamoyl radical optionally substituted on the alkyl moiety, an alkyl- or aryl-sulphonyl radical optionally substituted on the aryl moiety or an optionally substituted aminosulphonyl radical.

The compounds of the present invention show an antibacterial action superior to that of the known pyrido[2,3-d]pyrimidine-6-carboxylic acids.

The aryl radicals above-mentioned and mentioned hereinbelow are preferably phenyl or naphthyl radicals, are optionally monosubstituted, di-substituted or polysubstituted especially by halogen, preferably fluorine, chlorine and/or bromine, alkyl, alkoxy or alkylmercapto groups with 1 to 3 carbon atoms, an aryloxy (preferably phenoxy) or arylmercapto group (preferably phenyl mercapto), a trifluoromethyl, nitro or cyano group or a carboxylic acid ester group with 1 to 4 carbon atoms in the alcohol part.

According to the present invention there is further provided a process for the production of a compound of the present invention, in which (a) a pyrido[2,3-d]pyrimidine-6-carboxylic acid of the formula

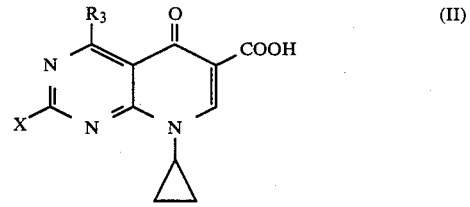

in which $R^3$ has the above-mentioned meaning and

X denotes a halogen atom or an alkylmercapto or alkoxy group with 1 to 4 carbon atoms, is reacted with an amines of the general formula

in which $R^1$ and $R^2$ have the above-mentioned meanings or (b) a pyrido[2,3-d]pyrimidine-6-carboxylic acid ester of the formula

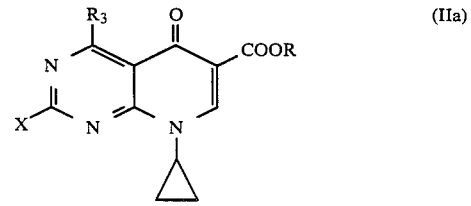

in which $R^3$ has the above-mentioned meaning,

R denotes an alkyl group and,

X denotes a halogen atom is reacted with an amine of formula (III) optionally in the presence of an acid-binding agent, for example, triethylamine or pyridine, and the resulting 2-aminopyrido[2,3-d]pyrimidine-6-carboxylic acid ester is then subjected to alkaline saponification, or (c) a 2-halogeno-4-(N-2-alkoxycarbonylalkyl-N-cyclopropyl)-amino-pyrimidine-5-carboxylic acid ester is reacted with an amine of the formula (III), the compound thus formed is subjected to cyclisation and the resulting product is dehydrogenated and saponified, or (d) a 2-halogeno-8-cyclopropyl-5-oxo-5,6,7,8-tetrahydropyrido[2,3-d]pyrimidine-6-carboxylic acid ester is reacted with an amine of the formula (III) and the resulting 2-amino-8-cyclopropyl-5-oxo-5,6,7,8-tetrahydro-pyrido[2,3-d]pyrimidine-6-carboxylic acid ester is dehydrogenated and saponified.

Reaction variant (c) is illustrated by the following reaction scheme in which the compounds of formula VIII is reacted with the amines of formula III under rigorous reaction conditions [with regard to the reaction conditions for the stepwise replacement of the two chlorine atoms of 2,4-dichloro-6-methyl-pyrimidine-5-carboxylic acid esters by amine radicals, compare Liebigs Ann. Chem. 1973, 1025–1035], the 2,4-diaminopyrimidinecarboxylic acid esters of formula (XI) are obtained. Subsequent Dieckmann cyclisation, dehydrogenation, for example, with bromine/triethylamine, and saponification then results in the 2-amino-pyrido[2,3-d]pyrimidine-6-carboxylic acids of the formula (I).

If, for example, 2-ethylmercapto-8-cyclopropyl-5-oxo-5,8-dihydro-pyrido[2,3-d]pyrimidine-6-carboxylic acid and N-methylpiperazine are used as the reactants, the course of the reaction variant can be illustrated by the following equation:

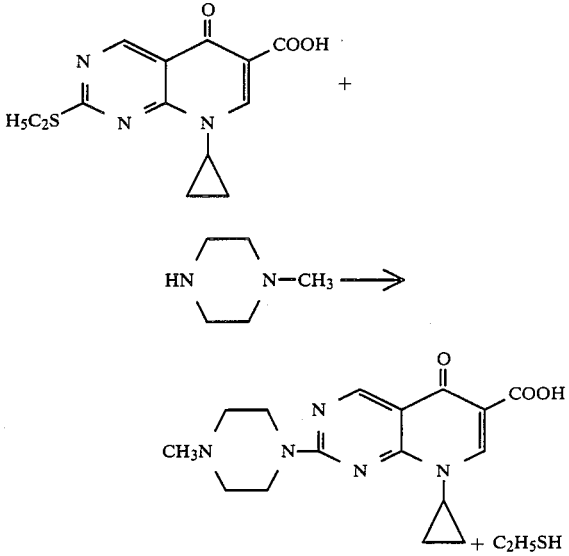

The starting compounds of formula (II) can be prepared by various processes:

(i) 4-chloro-pyrimidine-5-carboxylic acid chlorides which are substituted in the 2-position and have the formula (IV) are cycloaracylated with β-cyclopropylamino-acrylic acid esters of the formula (V) to give the esters corresponding to the carboxylic acids of the formula (II). Alkaline saponification of these esters gives the desired carboxylic acids of the formula (II).

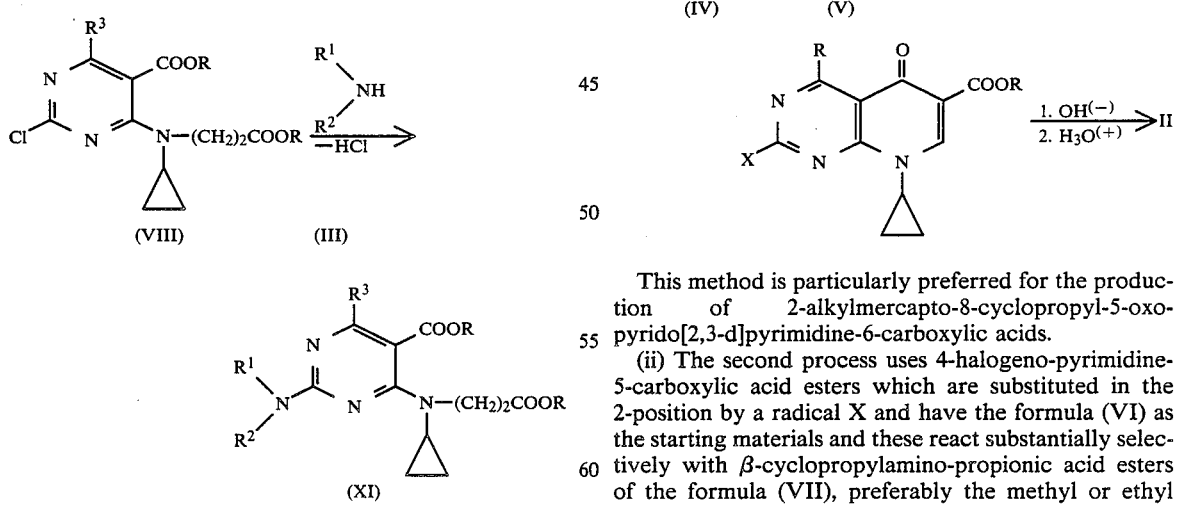

This method is particularly preferred for the production of 2-alkylmercapto-8-cyclopropyl-5-oxo-pyrido[2,3-d]pyrimidine-6-carboxylic acids.

(ii) The second process uses 4-halogeno-pyrimidine-5-carboxylic acid esters which are substituted in the 2-position by a radical X and have the formula (VI) as the starting materials and these react substantially selectively with β-cyclopropylamino-propionic acid esters of the formula (VII), preferably the methyl or ethyl esters, which are readily accessible by reaction of corresponding acrylic acid esters with cyclopropylamine, with replacement of the halogen atom in the 4-position by the amine radical, to give the monosubstitution product of the formula (VIII). In the presence of a strong base, such as, for example, potassium t-butanolate or sodium hydride, the latter are converted

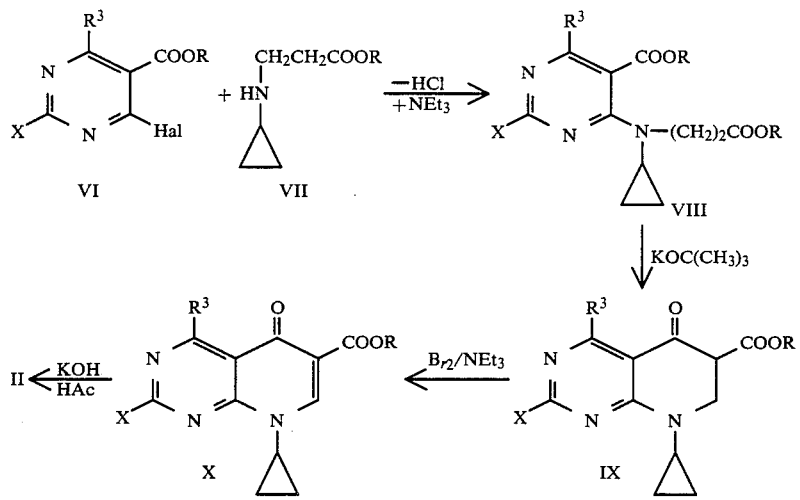

by Dieckmann cyclisation to the dihydro-pyrido[2,3-d]-pyrimidine-6-carboxylic acid esters of the formula (IX). When bromine or sulphuryl chloride and triethylamine or pyridine are used as the dehydrohalogenating agent, the carboxylic acid esters of the formula (X) are obtained from esters of formula (IX) and these can be saponified with alkali to give the carboxylic acids of the formula (II) (R denotes hydrogen).

If, on the other hand, the substituent X in compound of formula (X) represents a halogen atom, the compound of formula (X) is preferably converted by means of the amine of formula (III) to the carboxylic acid ester corresponding to formula (I) and this ester is then subjected to alkaline saponification to give the compounds in the present invention.

The dihydrocarboxylic acid esters of the formula (IX) in which $R^3$ denotes methyl can be dehydrogenated to esters of formula (X) only with chloranil or sulphur under the customary reaction conditions. In this case, bromine or sulphuryl chloride preferentially attacks the methyl group in the 4-position.

Diluents which can be used are inert organic solvents. These are preferably toluene, dioxane, dimethylformamide, dimethylsulphoxide and sulpholane. If the corresponding 2-halogeno-pyrido[2,3-d]pyrimidine-6-carboxylic acid esters are used in place of the 2-alkyl-mercapto-pyrido[2,3-d]pyrimidine-6-carboxylic acid esters, an acid-binding agent is preferably added. Acid-binding agents which can be used are preferentially alkali metal carbonates, alkali metal hydroxides and tertiary organic bases, for example, triethylamine and pyridine.

The reaction temperatures can vary within a relatively wide range. Preferably the reaction is carried out at between 20° and 180° C. and more preferably at between 60° and 140° C.

The reaction can be carried out under normal pressure or also under elevated pressure, especially in the case of gaseous and low-boiling amines of the formula (III). In general, the reaction is carried out under pressures of between 1 and 100 bars and preferably of between 1 and 10 bars.

When carrying out the lprocess, preferably 1 to 4 mols of amine and more preferably 1.5 to 2.5 mols of amine are employed per 1 mol of carboxylic acid.

New antibacterial active compounds of the present invention include: 2-methyl-amino-,2-dimethylamino-, 2-n-hexylamino-, 2-benzylamino-,2-(4-methoxybenzyl-amino)-, 2-pyrrolidino, 2-morpholino-,2-piperidino-,2-hexamethylene-imino, 2-piperazino-, 2-(4-methyl-piperazino)-,2-(4-benzylpiperazino)-, 2-(4-β-hydroxyethylpiperazino)-, 2-(4-p-methoxybenzylpiperazino)-,2-pyrrolidino-4-methyl- and 2-morpholino-4-methyl-8-cyclopropyl-5-oxo-5,8-dihydropyrido[2,3-d]pyrimidine-6-carboxylic acid and salts, especially alkali metal salts (particularly sodium or potassium salts) of these compounds. Additional salts of the invention are ammonium salts, acid addition salts with amino groups and amine addition salts with carboxylic acids. Thus, a resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactac, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluenesulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

It has been found that the compounds of the present invention possess outstanding antimicrobial properties and, moreover, act as growth regulators. In particular they have a broad bacteriostatic and bactericidal action against Gram-positive bacteria such as staphylococci and streptococci and Gram-negative bacteria, such as Escherichia, Proteus, Providencia, Enterobacter, Klebsiella and Psuedomonas. This list of pathogens is to be regarded merely as illustrative.

The improved antibacterial action of the new compounds according to the invention is particularly marked in the case of the compounds described hereinafter in Examples 1 and 7, which when compared with 2-piperazino-8-ethyl-5-oxo-5,8-dihydro-pyrido[2,3-d]pyrimidine-6-carboxylic acid ("pipemidic acid") or the known 1-ethyl-7-methyl-4-naphthyridone-(1,8)-3-carboxylic acid ("Nalidixinsäure" ([nalidixic acid"); Ehrhart/Ruschig, Arzneimittel, Volume 2: Chemotherapeutika, Verlag Chemie 1968, page 1,568) prove far superior in vitro and in vivo against bacteria as *Escherichia coli*, Proteus, Klebsiella and Pseudomonas.

The improved antibacterial activity of the compounds according to the invention makes it possible to use them as active compounds in medicine and they can be used for the treatment of systemic or local bacteria infections, in particular of diseases of the urogenital system. The provision of new bactericidal agents for combating bacteria which are resistant to known bactericidal agents is an advance in pharmacy.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit from comprising a compound of the invention.

The invention also provides a medicament in the form of tablets (including lozenges and granules), dragees, capsules, pills, ampoules or suppositories comprising a compound of the invention.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or submultiple (down to a fortieth) of a daily dose of the compounds of the invention in association with a carrier and/or enclosed within an envelope. Whenever the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution, e.g. paraffin; (f) resorption accelerators, e.g. quaternary ammonium compounds; (g) surface active agents, e.g. cetyl alcohol, glycerol monostearate; (h) absorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition. Preferably 10–200 mg of the active ingredient per kilogramm body weight are administered.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

The compounds according to the invention can also be used as feed additives to promote growth and to improve the feed utilisation in animal husbandry, especially in the husbandry of fattening animals. The active compounds are then preferably administered via the feed and/or the drinking water in concentrations of from 0,001 to 0,1%

The present invention also relates to agents which contain the compound of the present invention. These include, for example, feed concentrates for animal husbandry, which, in the customary manner, can also contain vitamins and/or mineral salts in addition to the active compounds, or pharmaceutical formulations. The present invention thus includes a medicated fodder comprising a compound of the present invention and a nutritious material.

The following Examples illustrate processes for the production of compounds of the present invention.

EXAMPLE 1

2-(4-Methyl-piperazino)-8-cyclopropyl-5-oxo-5,8-dihydropyrido[2,3-d]pyrimidine-6-carboxylic acid (formula (I) in which $R^1R^2N$=4-methylpiperazine and $R^3$=H).

A solution of 2.91 g of 2-ethylmercapto-8-cyclopropyl-5-oxo-5,8-dihydro-pyrido[2,3-d]pyrimidine-6-carboxylic acid and 2.21 g of N-methylpiperazine in 30 ml of N-dimethylformamide is heated at 110° for 2.5 hours. The solvent is distilled off in vacuo and the residue is recrystallised from ethanol. 2.4 g (73% of the theoretical yield) of 2-(4-methyl-piperazino-8-cyclopropyl-5-oxo-5,8-dihydro-pyrido[2,3-d]pyrimidine-6-carboxylic acid with a melting point of 209°–210° C. are obtained.

EXAMPLES 2 TO 54

The carboxylic acids of Examples 2 to 54 were obtained by a procedure analogous to that of Example 1. They are listed in Table 1. The substituent positions of radicals $R^1$, $R^2$ and $R^3$ are as given in formula (I).

TABLE 1

| Example No. | $R^1$ | $R^2$ | $R^3$ | Decomposition Temp. (°C.) |
|---|---|---|---|---|
| 2 | | —CH$_2$CH$_2$CH$_2$CH$_2$— | CH$_3$ | 253 |
| 3 | | —(CH$_2$)$_2$O(CH$_2$)$_2$— | CH$_3$ | 270 |
| 4 | | —CH$_2$CH$_2$CH$_2$CH$_2$— | H | 306 |
| 5 | | —(CH$_2$)$_2$O(CH$_2$)$_2$— | H | 354 |
| 6 | | —CH$_2$(CH$_2$)$_3$CH$_2$— | H | 252 |
| 7 | | —(CH$_2$)$_2$—N(H)—(CH$_2$)$_2$— | H | 246 |
| 8 | | —(CH$_2$)$_2$—N((CH$_2$)$_2$CH)—(CH$_2$)$_2$— | H | 176* |
| 9 | | —(CH$_2$)$_2$—N(C$_6$H$_4$OCH$_3$)—(CH$_2$)$_2$— | H | 232 |
| 10 | | —(CH$_2$)$_2$—N(COOC$_2$H$_5$)—(CH$_2$)$_2$ | H | 250 |
| 11 | CH$_3$ | CH$_3$ | H | 228** |
| 12 | | —(CH$_2$)$_2$—N(SO$_2$N(CH$_3$)$_2$)—(CH$_2$)$_2$— | H | 302 |
| 13 | | —(CH$_2$)$_2$—CH(C$_2$H$_5$)—(CH$_2$)$_2$— | H | 207 |
| 14 | | —CH$_2$CH$_2$(CH$_2$)$_2$CH$_2$CH$_2$— | H | 227 |
| 15 | | —CH$_2$—C(CH$_3$)$_2$—C(CH$_3$)$_2$—CH$_2$— | H | 277 |
| 16 | | —CH$_2$C(CH$_3$)$_2$—(CH$_2$)$_2$— | H | 267 |
| 17 | | —CH$_2$—C(CH$_3$)$_2$—(CH$_2$)$_3$— | H | 170 |
| 18 | | —(CH$_2$)$_2$—CH(CH$_3$)—(CH$_2$)$_2$— | H | 212 |

TABLE 1-continued

| Example No. | R¹ | R² | R³ | Decomposition Temp. (°C.) |
|---|---|---|---|---|
| 19 | | $-(CH_2)_2-N(-(CH_2)_2C_6H_5)-(CH_2)_2-$ | H | 229 |
| 20 | | $-(CH_2)_2CH=CH-CH_2-$ | H | 245 |
| 21 | | $-(CH_2)_2C(CH_3)=CH-CH_2-$ | H | 197 |
| 22 | | $-(CH_2)_2-C(CH_3)_2-(CH_2)_2-$ | H | 276 |
| 23 | | $-(CH_2)_2-C(n\text{-}C_8H_{17})=CH-CH_2-$ | H | 138 |
| 24 | | $-(CH_2)_2-N(CH_2-C_6H_5)-(CH_2)_2-$ | H | 226 |
| 25 | | $-(CH_2)_2-N(O=C-CH(CH_3)_2)-(CH_2)_2-$ | H | 228 |
| 26 | | $-(CH_2)_2-C(n\text{-}C_4H_9)=CH-CH_2-$ | H | 173 |
| 27 | | $-(CH_2)_2-N(C_6H_5)-(CH_2)_2-$ | H | 252 |
| 28 | | $-(CH_2)_2-N(2,5\text{-dimethylphenyl})-(CH_2)_2-$ | H | 217 |
| 29 | | $-(CH_2)_2-N(2\text{-methoxyphenyl})-(CH_2)_2-$ | H | 265 |
| 30 | | $-(CH_2)_2-N(CHO)-(CH_2)_2-$ | H | 285 |
| 31 | | $-(CH_2)_2-N(2\text{-nitrophenyl})-(CH_2)_2-$ | H | 232 |
| 32 | H | $CH_3$ | H | 282** |
| 33 | | $-(CH_2)_2-N(1\text{-naphthyl})-(CH_2)_2-$ | H | 262 |
| 34 | | $-(CH_2)_2-N(2,6\text{-dimethylphenyl})-(CH_2)_2-$ | H | 218 |
| 35 | | $-(CH_2)_2-N(COOCH_2C_6H_5)-(CH_2)_2-$ | H | 235 |
| 36 | | $-CH_2-CH(CH_3)-N(C_2H_5)-CH(CH_3)-CH_2-$ | H | 142 |
| 37 | | $-(CH_2)_3-CH(OH)-CH_2-$ | H | 287 |
| 38 | | $-(CH_2)_2-CH(OH)-(CH_2)_2-$ | H | 215 |
| 39 | | $-(CH_2)_2-N(3,4\text{-dichlorophenyl})-(CH_2)_2-$ | H | 232 |
| 40 | | $-(CH_2)_2-N(3\text{-CF}_3\text{-phenyl})-(CH_2)_2-$ | H | 237 |
| 41 | | $-(CH_2)_2-N(2\text{-pyridyl})-(CH_2)_2-$ | H | 314 |
| 42 | $CH_3(CH_2)_5-$ | H | H | 177 |
| 43 | $CH_3$ | $-CH_2CH_2CH$ | H | 194 |
| 44 | $H_2C=CH-CH_2-$ | H | H | 265 |
| 45 | $CH_3(CH_2)_{11}-$ | H | H | 187 |
| 46 | | $-(CH_2)_2-C(CH_3)=C(CH_3)-CH_2-$ | H | 247 |
| 47 | $(C_2H_5)_2N-CH_2CH_2-$ | H | H | 176 |
| 48 | $CH_3OCH_2CH_2-$ | H | H | 265 |
| 49 | | $-CH_2-CH_2-S-CH_2-$ | H | 284 |
| 50 | | $-CH_2CH(COOC_2H_5)-(CH_2)_3-$ | H | 163 |
| 51 | | $-(CH_2)_2-N((CH_2)_3OH)-(CH_2)_2-$ | H | 190 |
| 52 | | $-(CH_2)_2-CH(COOC_2H_5)-(CH_2)_2-$ | H | 222 |
| 53 | | $-(CH_2)_2-N(4\text{-hydroxyphenyl})-(CH_2)_2-$ | H | 299 |

TABLE 1-continued

| Example No. | R$^1$ | R$^2$ | R$^3$ | Decomposition Temp. (°C.) |
|---|---|---|---|---|
| 54 | —(CH$_2$)$_2$—N—(CH$_2$)$_2$— 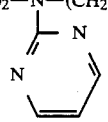 | | H | 342 |
| 55 | —(CH$_2$)$_2$—S—(CH$_2$)$_2$— | | H | 309 |

*Was isolated as the N—hydroxyethyl-piperazine salt.
**The gaseous amine was passed into the solution of the 2-alkylmercapto-pyrido[2,3-d]pyrimidine-carboxylic acid for 3 hours at 110° C.

The 2-alkylmercapto-8-cyclopropyl-5-oxo-5,8-dihydro-pyrido[2,3-d]pyrimidine-6-carboxylic acids used as the starting materials can be synthesized by two different routes:

(A) By the intermediate-product on route (i) given hereinbefore.

(B) In a multi-stage reaction sequence, for example using 4-chloro-2-ethylmercapto-pyrimidine-5-carboxylic acid ethyl ester as the starting material.

(1) Z-Ethylmercapto-4-(N-2-ethoxycarbonylethyl-N-cyclopropyl)-amino-pyrimidine-5-carboxylic acid ethyl ester (a compound of formula (VIII) in which R=ethyl, X=ethylmercapto and R$^3$=H).

A mixture of 78.5 g of β-cyclopropylaminopropionic acid ethyl ester and 50.5 g of triethylamine is added dropwise at a rapid rate at ∼10° C. to a solution of 123 g of 4-chloro-2-ethylmercapto-pyrimidine-5-carboxylic acid ethyl ester in 400 ml of cyclohexane, with ice-cooling and whilst stirring. The ice bath is removed and the temperature rises to ∼35° C. The reaction mixture is then left to stand overnight at room temperature and is washed with water and dried over Na$_2$SO$_4$ and the solvent is distilled off in vacuo. 168.1 g of the title compound are obtained in the form of a pale yellow oil. The β-cyclopropylaminopropionic acid ethyl ester used as a reactant is prepared as follows:

100 g of freshly distilled acrylic acid ethyl ester which has been cooled to −60° C. are added dropwise in the course of about 3 hours to a solution, which has been cooled to −60° to −70° C., of 57 g of cyclopropylamine in 150 ml of ethanol. The mixture is then allowed to warm slowly overnight to room temperature, the solvent is distilled off in vacuo and the residue is then subjected to fractionation. 122 g of β-cyclopropylamino-propionic acid ethyl ester pass over at 104°–110° C./22 mm Hg.

(2) 2-Ethylmercapto-8-cyclopropyl-5-oxo-5,6,7,8-tetrahydro-pyrido[2,3-d]pyrimidine-6-carboxylic acid ethyl ester (a compound of formula (IX) in which R=ethyl, X=ethylmercapto and R$^3$=H).

168.1 g of crude 2-ethylmercapto-4-(N-2-ethoxycarbonylethyl-N-cyclopropyl)-amino-pyrimidine-5-carboxylic acid ethyl ester are dissolved in 600 ml of anhydrous toluene, and 61.5 g of potassium tert.-butanolate are added rapidly, whilst stirring. The mixture is left to stand overnight, 35 g of glacial acetic acid and 200 ml of water are added, the phases are separated, the toluene solution is again washed with water and dried over Na$_2$SO$_4$ and the toluene is stripped off in vacuo. 168.1 g of the carboxylic acid ester are obtained. A sample recrystallised from cyclohexane melts at 86°–89° C.

(3) 2-Ethylmercapto-8-cyclopropyl-5-oxo-5,8-dihydropyrido[2,3-d]pyrimidine-6-carboxylic acid ethyl ester (a compound of formula (X) in which R=ethyl, X=ethylmercapto and R$^3$=H).

168.1 g of the tetrahydro-pyrido-pyrimidine-6-carboxylic acid ethyl ester prepared according to 2) are dissolved in 400 ml of chloroform, and a solution of 80 g of bromine in 40 ml of chloroform is added rapidly dropwise at ∼10°–15° C., with ice-cooling. The resulting mixture is then stirred for a further 10 minutes at ∼10° C., 120 g of triethylamine are added in the course of about 10 minutes and the ice bath is removed, whereupon the temperature rises to about 60°–65° C. The reaction mixture is stirred for a further 1.5 hours, washed twice with cold water and dried over sodium sulphate, the solvent is distilled off in vacuo and the residue is recrystallized from isopropyl alcohol. 156 g of 2-ethylmercapto-8-cyclopropyl-5-oxo-5,8-dihydropyrido[2,3-d]pyrimidine-6-carboxylic acid ethyl ester with a melting point of 138° C. are obtained.

(4) 2-Ethylmercapto-8-cyclopropyl-5-oxo-5,8-dihydropyrido[2,3-d]pyrimidine-6-carboxylic acid (a compound of formula (II) in which R=H, X=ethylmercapto and R$^3$=H).

A solution of 20 g of potassium hydroxide in 500 ml of water is added to 110 g of the ester prepared according to (3). The mixture is heated at 85°–95° C. for 30 minutes, whilst stirring, the resulting solution is filtered at room temperature and the filtrate is acidified with 25 g of glacial acetic acid. The precipitate is filtered off, washed with water and dried over calcium chloride in a vacuum drying cabinet. 85.3 g of pyrido[2,3-d]pyrimidine-6-carboxylic acid which has a melting point of 228°–230° C. and is sufficiently pure for the further reactions are obtained. A sample recrystallised from ethanol has a melting point of 235°–236° C.

The corresponding 2-methylmercapto-8-cyclopropyl-5-oxo-5,8-dihydro-pyriido[2,3-d]pyrimidine-6-carboxylic aciid with a melting point of 251° C. is also prepared in comparable yield by the same process.

EXAMPLE 56

2-Piperidino-8-cyclopropyl-5-oxo-5,8-dihydro pyrido[2,3-d]pyrimidine-6-carboxylic acid (a compound of formula (I) in which R$^1$R$^2$N=piperidine and R$^3$=H).

18 g of piperidine (or 8.6 g of piperidine and 11 g of triethylamine) are added dropwise to a solution of 29.3 g of 2-chloro-8-cyclopropyl-5-oxo-5.8-dihydropyrido[2,3-d]pyrimidine-6-carboxylic acid ethyl ester in 150 ml of anhydrous toluene, with ice-cooling and whilst stirring. The mixture is heated at the boil for 1 hour under reflux, the solvent is distilled off in vacuo the residue is taken up in water, the precipitate is filtered off and suspended in 50 ml of ethanol, and a solution of 6.2 g of potassium hydroxide in 80 ml of water is added. The mixture is then heated at the boil under reflux for 2.5 hours, the alcohol is distilled off in vacuo, about 100 ml of H$_2$O are added to the residue, the mixture is filtered and the filtrate is acidified with glacial acetic acid. The precipitate is filtered off, washed with H$_2$O and dried over CaCl$_2$ at 80°–100° C. in a vacuum drying cabinet. After recrystallisation from ethanol, 26.7 g of 2-piperidino-8-cyclopropyl-5-oxo-5,8-dihydropyrido[2,3-d]pyrimidine-6-carboxylic acid with a melting point of 250°–252° C. are obtained.

All of the compounds in Table 1 with the exception of the 2-piperazino derivative of Example 7 can be prepared by this process, because piperazine reacts with the 2-chloro-8-cyclopropyl-5-oxo-5,8-dihydropyrido[2,3-d]pyrimidine-6-carboxylic acid methyl ester to give a mixture of the mono- and di-substitution products.

The 2-chloro-8-cyclopropyl-5-oxo-5,8-dihydropyrido[2,3-d]pyrimidine-6-carboxylic acid ethyl ester used as the starting material can be prepared in 3 stages using 2,4-dichloro-pyrimidine-5-carboxylic acid ethyl ester as the starting material:

(1) 2-Chloro-4-(N-2-ethoxycarbonylethyl-N-cyclopropyl)-amino-pyrimidine-5-carboxylic acid ethyl ester (a compound of formula (VIII) in which X=chlorine, R=ethyl, and $R^3$=H).

A mixture of 15.7 g of β-cyclopropylaminopropionic acid ethyl ester and 10.1 g of triethylamine is added dropwise at 10°–15° C. to a solution of 22.1 g of 2,4-dichloro-pyrimidine-5-carboxylic acid ethyl ester in 150 ml of anhydrous cyclohexane, with ice-cooling and whilst stirring. The mixture is stirred for 1 hour at 10°–15° C., left to stand overnight at room temperature, washed with water and dried over sodium sulphate and the solvent is distilled off in vacuo. 34.1 g of the above ester are obtained in the form of a non-crystallising pale yellow oil.

The 6-methyl compound (a compound of formula (VIII) in which X=chlorine, R=ethyl and $R^3$=CH$_3$) was prepared correspondingly, using 2,4-dichloro-6-methyl-pyrimidine-5-carboxylic acid ethyl ester as the starting material.

(2) 2-Chloro-8-cyclopropyl-5-oxo-5,6,7,8-tetrahydropyrido[2,3-d]pyrimidine-6-carboxylic acid ethyl ester (a compound of formula (IX) in which R=ethyl, X=chlorine and $R^3$=H).

11.2 g of potassium tert.-butanolate are added in portions to a solution of 34.1 g of 2-chloro-4-(N-2-ethoxycarbonlethyl-N-cyclopropyl)-amino-pyrimidine-5-carboxylic acid ethyl ester in 250 ml of anhydrous toluene, with ice-cooling and whilst stirring. The mixture is stirred for 5 hours at room temperature, 150 ml of ice-water are added, the resulting mixture is acidified with 4N HCl, the phases are separated, the product phase is dried over Na$_2$SO$_4$ and the solvent is stripped off in vacuo. 25 g of crude product are obtained and this is employed direct in the next reaction stage.

The corresponding 4-methyl-pyrido[2,3-d]pyrimidine-carboxylic acid ethyl ester (a compound of formula (IX) in which R=ethyl, X=chlorine and $R^3$=CH$_3$) melts at 110°–112° C. after recrystallisation from toluene/light benzine.

(3) 2-Chloro-8-cyclopropyl-5-oxo-5,8-dihydropyrido[2,3-d]pyrimidine-6-carboxylic acid ethyl ester (a compound of formula (X) in which R=ethyl, X=chlorine and $R^3$=H).

25 g of the compound described above having the formula (IX) where $R^3$=H, are dissolved in 100 ml of chloroform, and a solution of 11.7 g of bromine in 40 ml of chloroform is added dropwise at 0°–10° C., with ice-cooling and whilst stirring. The mixture is stirred for 30 minutes at ∼10° C., 15 g of triethylamine are added slowly dropwise at 10°–15° C. and the reactor mixture is stirred for a further 1 hour with ice-cooling and is then stirred for 6 hours at room temperature. The reaction mixture is washed with ice-water and dried over sodium sulphate and the solvent is stripped off in vacuo. After recrystallisation of the residue from toluene/cyclohexane, 16 g of 2-chloro-8-cyclopropyl-5-oxo-5,8-dihydro-pyrido[2,3-d]pyrimidine-6-carboxylic acid ethyl ester with a melting point of 169° C. are obtained.

EXAMPLE 57

2-Pyrrolidino-8-cyclopropyl-5-oxo-5,8-dihydropyrido[2,3-d]pyrimidine-6-carboxylic acid (a compound of formula (I) in which $R^1R^2N$=pyrrolidino and $R^3$=H).

7.8 g of pyrrolidine are added dropwise to a solution of 17.1 g of 2-chloro-4-(N-2-ethoxycarbonylethyl-N-cyclopropyl)-amino-pyrimidine-5-carboxylic acid ethyl ester in 100 ml of anhydrous toluene, the temperature of the solution rising to ∼40°–50° C. during the addition. The reaction mixture is stirred for 30 minutes and boiled under reflux for 30 minutes, the cooled solution is washed with H$_2$O and dried over Na$_2$SO$_4$ and the solvent is distilled off in vacuo and 18.5 g of crude 2-pyrrolidino-4-(N-2-ethoxycarbonylethyl-N-cyclopropyl)-amino-pyrimidine-5-carboxylic acid ethyl ester are obtained; this is dissolved in 120 ml of toluene, and 6.5 g of potassium tert.-butanolate are added rapidly in portions. The mixture is left to stand overnight at room temperature, 100 ml of water and 3.5 g of glacial acetic acid are added, the toluene phase is separated off, washed with H$_2$O and dried over Na$_2$SO$_4$, and the solvent is stripped off in vacuo. After recrystallisation from cyclophexane, 12.5 g of 2-pyrrolidino-8-cyclopropyl-5-oxo-5,6,7,8-tetrahydro-pyrido[2,3-d]pyrimidine-6-carboxylic acid ethyl ester with a melting point of 72°–74° C. are obtained; this is dissolved in 150 ml of chloroform, and a solution of 6.2 g of bromine in 20 ml of CHCl$_3$ is added dropwise with ice-cooling and whilst stirring. The mixture is stirred for 2 hours at room temperature, 8.5 g of triethylamine are added dropwise with ice-cooling and whilst stirring, the resulting mixture is stirred for 1 hour at room temperature and for 1 hour at 50° C., washed with water and dried over Na$_2$SO$_4$ and the solvent is distilled off in vacuo. 11.5 g of 2-pyrrolidino-8-cyclopropyl-5-oxo-5,8-dihydro-pyrido[2,3-d]pyrimidine-6-carboxylic acid ethyl ester are obtained and, for saponification, 50 ml of ethanol and a solution of 5 g of potassium hydroxide in 100 ml of water are added to this. The mixture is heated at the boil under reflux for 2 hours, the alcohol is distilled off as completely as possible in vacuo, the carboxylic acid salt is brought into solution with H$_2$O, the solution is filtered and the filtrate is acidified to pH 5 with glacial acetic acid. The precipitate is filtered off, washed with H$_2$O and dried over CaCl$_2$ at 80°–100° C. in a vacuum drying cabinet. After recrystallisation from dimethylformamide/ethanol, 9.2 g of 2-pyrrolidino-8-cyclopropyl-5-oxo-5,8-dihydro-pyrido[2,3-d]pyrimidine-6-carboxylic acid with a decomposition temperature of 306° C. are obtained. (Example 4 (in Table 1)).

2-Piperidino- and 2-morpholino-8-cyclopropyl-5-oxo-5,8-dihydro-pyrido[2,3-d]pyrimidine-6-carboxylic acid (Examples 6 and 5 (in Table 1)) are also prepared by the same process.

EXAMPLE 58

2-Pyrrolidino-4-methyl-8-cyclopropyl-5-oxo-5,8-dihydro-pyrido[2,3-d]pyrimidine-6-carboxylic acid (a compound of formula (I) in which $R^1R^2N$=pyrrolidino and $R^3$=CH$_3$).

100 ml of toluene and 2.5 g of chloranil are added to 3.4 g of 2-pyrrolidino-4-methyl-8-cyclopropyl-5-oxo-5,6,7,8-tetrahydro-pyrido[2,3-d]pyrimidine-6-carboxylic acid ethyl ester. The mixture is warmed at 80°–90° C. for 30 minutes, the solvent is stripped off in vacuo and the residue is recrystallised from acetonitrile. The resulting 2.2 g of the ester with a melting point of 170°–175° C. are heated with 20 ml of ethanol and a solution of 1.2 g of potassium hydroxide in 60 ml of H₂O for 2.5 hours at the boil under reflux. The alcohol is distilled off, the filtered solution is acidified with glacial acetic acid and the precipitate is filtered off, washed with water and dried. 1.6 g of 2-pyrrolidino-4-methyl-8-cyclopropyl-5-oxo-5,8-dihydro-pyrido[2,3-d]pyrimidine-6-carboxylic acid with a melting point of 253° C. are obtained. (Example 2 (in Table 1)).

The compound of Example 3 (in Table 1) is also prepared by the same process.

The 2-pyrrolidino-4-methyl-8-cyclopropyl-5-oxo-5,6,7,8-tetrahydro-pyrido[2,3-d]pyrimidine-6-carboxylic acid ethyl ester used as the starting material is prepared as follows: 31 g of 2-chloro-4-methyl-8-cyclopropyl-5-oxo-5,6,7,8-tetrahydro-pyrido[2,3-d]pyrimidine-6-carboxylic acid ethyl ester are dissolved in 300 ml of toluene, and 20 g of pyrrolidine are added rapidly dropwise, the temperature rising to about 40° C. The mixture is heated at the boil under reflux for 30 minutes, washed with water and dried over Na₂SO₄ and the solvent is stripped off in vacuo. The residue is recrystallised from wash benzine (boiling point 110°–140° C.). 30 g of colourless crystals with a melting point of 121°–123° C. are obtained.

Among the new 2-amino-8-cyclopropyl-5-oxo-5,8-dihydro-pyrido[2,3-d]pyrimidine-6-carboxylic acid salts of the invention, those salts that are pharmaceutically acceptable are particularly important and are preferred. Especially preferred are the alkali metal or alkaline earth metal salts.

The new free 2-amino-8-cyclopropyl-5-oxo-5,8-dihydro-pyrido[2,3-d]pyrimidine-6-carboxylic acid compounds of the general formula (I) and their salts can be interconverted in any suitable manner; methods for such interconvertion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal is converted in the patient's body to the active compound.

What is claimed is:

1. A compound of the formula

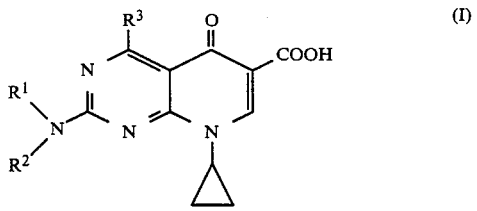

or a therapeutically useful acid-addition salt thereof, in which $R^1$ is alkyl having 1 to 12 carbon atoms, optionally substituted by alkoxy having 1 to 4 carbon atoms or dialkylamino having 1 to 3 carbon atoms per alkyl radical; or alkenyl having 2 to 12 carbon atoms, $R^2$ is hydrogen; alkyl having 1 to 12 carbon atoms or hydroxyalkyl having 1 to 12 carbon atoms;

$R^1$ and $R^2$ taken together with the nitrogen atom on which they are substituents and, optionally, with a further hetero atom selected from oxygen, sulphur or $NR_4$, form a 5- to 7-membered ring which is optionally substituted on a carbon atom by 1 to 4 $C_1$–$C_2$-alkyl groups, $R^4$ is hydrogen; $C_1$ to $C_6$ alkyl, optionally substituted by hydroxy, alkoxy, alkylmercapto or dialkylamino group with 1 to 3 carbon atoms per alkyl radical or alkoxycarbonyl with 1 to 4 carbon atoms in the alkoxy moiety; cycloalkyl with 3 to 7 carbon atoms; phenylalkyl which has up to 4 carbon atoms in the aliphatic part and is unsubstituted or substituted in the phenyl part by halogen, $C_1$–$C_3$-alkyl, $C_1$–$C_3$-alkoxy, $C_1$–$C_3$-alkylmercapto, phenoxy, phenylmercapto, trifluoromethyl, nitro, cyano or carboxylic acid ester with 1 to 4 carbon atoms in the alcohol part; phenyl or pyridyl, pyrimidyl, thiazolyl or benzthiazolyl or alkoxycarbonyl which has 1 to 4 carbon atoms in the alkoxy moiety; or alkanoyl with 1 to 6 carbon atoms; phenylcarbonyl; or aminosulphonyl; and $R^3$ is hydrogen or alkyl having up to 3 carbon atoms.

2. A compound according to claim 1 in which the 5-membered to 7-membered ring formed by $R^1$ and $R^2$ together with the nitrogen atom on which they are substituents includes as a ring member, oxygen, sulphur, or $NR^4$ in which $R^4$ has the same meaning as in claim 1.

3. A compound according to claim 1 or 2 in which $R^4$ denotes a pyridine, pyrimidine, thiazole or benzthiazole radical.

4. A compound according to claim 1 which is 2-(4-methylpiperazino)-8-cyclopropyl-5-oxo-5,8-dihydropyrido[2,3-d]pyrimidine-6-carboxylic acid.

5. A compound according to claim 1 which is 2-pyrrolidino-8-cyclopropyl-5-oxo-5,8-dihydropyrido[2,3-d]pyrimidine-6-carboxylic acid.

6. A compound according to claim 1 which is 2-morpholino-8-cyclopropyl-5-oxo-5,8-dihydropyrido[2,3-d]pyrimidine-6-carboxylic acid.

7. A compound according to claim 1 which is 2-piperidino-8-cyclopropyl-5-oxo-5,8-dihydropyrido[2,3-d]pyrimidine-6-carboxylic acid.

8. A compound according to claim 1 which is 2-piperazino-8-cyclopropyl-5-oxo-5,8-dihydropyrido[2,3-d]pyrimidine-6-carboxylic acid.

9. A compound according to claim 1 which is 2-(4-β-hydroxyethyl-piperazino)-8-cyclopropyl-5-oxo-5,8-dihydropyrido [2,3-d]pyrimidine-6-carboxylic acid.

10. A compound according to claim 1 which is 2-dimethylamino-8-cyclopropyl-5-oxo-5,8-dihydropyrido[2,3-d]pyrimidine-6-carboxylic acid.

11. A compound according to claim 1 which is 2-4-formyl-piperazino 8-cyclopropyl-5-oxo-5,8-dihydropyrido[2,3-d]pyrimidine-6-carboxylic acid.

* * * * *